United States Patent [19]

Itakura

[11] 4,401,796

[45] Aug. 30, 1983

[54] SOLID-PHASE SYNTHESIS OF POLYNUCLEOTIDES

[75] Inventor: Keiichi Itakura, Arcadia, Calif.

[73] Assignee: City of Hope Research Institute, Duarte, Calif.

[21] Appl. No.: 258,924

[22] Filed: Apr. 30, 1981

[51] Int. Cl.$^3$ .............................................. C08F 8/40
[52] U.S. Cl. .................................... 525/340; 525/375; 525/333.3; 525/333.6; 536/23; 536/24; 536/28; 536/29
[58] Field of Search ....................... 525/366, 340, 375; 521/32; 536/22, 23, 24, 25, 26, 27, 28, 29

[56] References Cited

U.S. PATENT DOCUMENTS

| | | | |
|---|---|---|---|
| 3,985,690 | 10/1976 | Dean | 536/22 |
| 4,037,037 | 7/1977 | Patchornik et al. | 525/366 |
| 4,043,948 | 8/1977 | Rayskys et al. | 525/366 |
| 4,066,827 | 1/1978 | Seita | 525/375 |
| 4,217,421 | 8/1980 | Beasley | 521/32 |
| 4,276,395 | 6/1981 | Vollhardt et al. | 525/366 |

*Primary Examiner*—Paul R. Michl
*Attorney, Agent, or Firm*—Ellsworth R. Roston; Charles H. Schwartz

[57] ABSTRACT

A resin support formed from a suitable resin such as polystyrene or a silica gel may be provided by forming an amino resin and by reacting the amino resin with an activated ester of a nucleoside to obtain the dimethoxytrityl resin. To add each successive nucleotide to the resin support, the nucleoside is phosphorylated to provide a monotriazolide. The phosphorylation may be provided by the reaction of a phosphoditriazolide with a 3'-hydroxyl neucleoside. The dimethoxytrityl resin is then hydroxylated to substitute the hydroxyl group for the dimethoxytrityl group in the resin support. The monotriazolide is then reacted with the hydroxylated resin support to provide the dimethoxytrityl resin. This reaction may occur in the presence of a nucleophilic catalyst, such as a catalyst selected from a group consisting of dimethylaminopyridine, N'-methylimidazole and tetrazole. A hydroxyl group may be then substituted again for the dimethoxytrityl group in the dimethoxytrityl resin to provide for the addition of other nucleotides to the resin support. The procedure may be repeated to provide polynucleotides with extended chains of nucleotides.

51 Claims, 5 Drawing Figures

| STEP | SOLVENT OR REAGENT | AMOUNT | SHAKING TIME (MIN) | NUMBER OF OPERATIONS |
|---|---|---|---|---|
| 1 | PYRIDINE | 10 ml | 1 | 2 |
| 2 | 10% SOLUTION OF $Ac_2O$ IN PYRIDINE | 10 ml | 60 | 1 |
| 3 | PYRIDINE | 10 ml | 1 | 2 |
| 4 | $CHCl_3$-MeOH (7:3 v/v, 0°C SOLUTION) | 10 ml | 1 | 3 |
| 5 | 2% BSA (0°C SOLUTION) | 10 ml | 1 | 2 |
| 6 | $CHCl_3$-MeOH (7:3 v/v) | 10 ml | 1 | 2 |
| 7 | PYRIDINE | 10 ml | 1 | 2 |
| 8 | PYRIDINE | 10 ml | CO-EVAPORATION | 1 |
| 9 | MONOMER SOLUTION IN THF (0.125 MOLE SOLUTION) | 5 ml | 60-120 | 1 |

Fig. 3

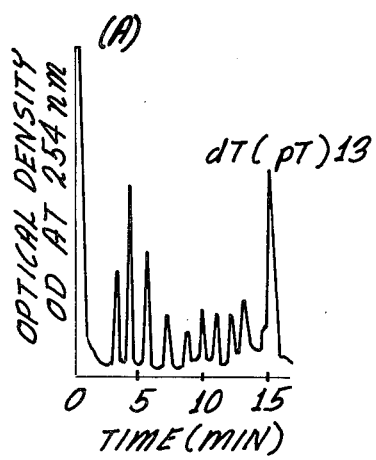
(A) dT(pT)13

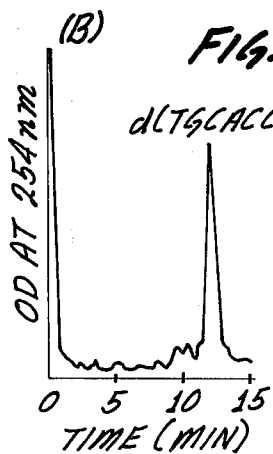
(B) d(TGCACCATTCT)

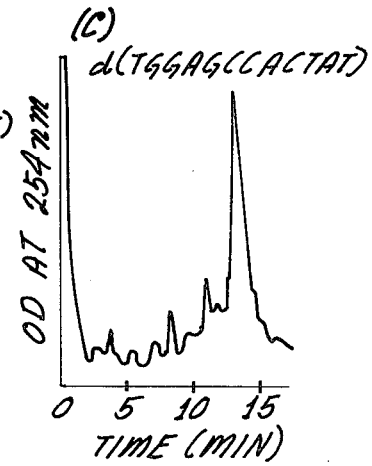
(C) d(TGGAGCCACTAT)

Fig. 4

| YIELD[a] | CYCLE | | | | | | | | | | | | | OVERALL YIELD |
|---|---|---|---|---|---|---|---|---|---|---|---|---|---|---|
| | 1 | 2 | 3 | 4 | 5 | 6 | 7 | 8 | 9 | 10 | 11 | 12 | 13 | |
| dT14 | 96 | 91 | 92 | 88 | 83 | 83 | 91 | 76 | 91 | 83 | 80 | 100 | 95 | 19 |
| DODECAMER[b] | 85 | 99 | 95 | 98 | 94 | 93 | 86 | 82 | 92 | 87 | 100 | | | 39 |
| UNDECAMER[b] | 99 | 93 | 99 | 95 | 92 | 100 | 96 | 91 | 91 | 97 | | | | 61 | a YIELDS WERE ESTIMATED BY THE QUANTITATIVE ANALYSIS OF DIMETHOXYTRITYL FUNCTION LIBERATED FROM THE RESIN AFTER STEP 5 b COUPLING REACTION ON THE MERRIFIELD RESIN IN THF.

Fig. 5

SOLID-PHASE SYNTHESIS OF POLYNUCLEOTIDES

This invention relates to methods of producing polynucleotides in a relatively simple and efficient manner. The invention also relates to resin supports and to polynucleotides produced by such methods.

The synthesis of polynucleotides has become important in recent years in the synthesis of DNA. By such synthesis of DNA, life-saving chemicals such as insulin can be formulated artifically. Such artifical formulations will provide for a more efficient production of the material than the methods of the prior art. Other materials will hopefully also be formulated for the benefit of mankind by restructuring the DNA.

In order to synthesize the DNA, polynucleotides of particular sequence often have to be provided. These polynucleotides have had to be formulated through progressive cycles of chemical reactions. When a support has been used, a nucleoside has been added to the support in the first cycle. This support has preferably been a resin support such as polystyrene. In subsequent cycles, mononucleotides, dinucleotides or trinucleotides have been added to the support. The addition of the mononucleotides, dinucleotides or trinucleotides to the support in each cycle has been relatively slow and inefficient.

A considerable effort has been made in recent years to provide a method of improving the efficiency, and shortening the time, of adding the monocucleotides, dinucleotides and trinucleotides to the resin support after a nucleoside has been added to the resin support in the first cycle of operation. Such methods have been partially successful but the efficiency and the time of adding such nucleotides have still been subject to improvement.

This invention provides an improved method of adding mononucleotides, dinucleotides and trinucleotides to a resin support after a mononucleoside has been first added to the resin support. In this way, polynucleotides having any desired number of nucleotides can be easily and efficiently formed.

In the method of this invention, a resin support formed from a suitable resin such as a polystyrene or a silica gel may be provided by forming an amino resin and by combining the amino resin with an activated ester of a nucleoside to obtain the dimethoxytrityl resin. To add each successive nucleotide to the resin support, the nucleoside is phosphorylated to provide a monotriazolide. The phosphorylation may be provided by the reaction of a phosphotriazolide with a 3'-hydroxyl nucleoside. The dimethoxytrityl resin is then hydroxylated to substitute the hydroxyl group for the dimethoxytrityl group in the resin support.

The monotriazolide is reacted with the hydroxylated resin support to provide the dimethoxytrityl resin. This reaction may occur in the presence of a nucleophilic catalyst such as a material selected from a group consisting of dimethylaminopyridine N'-methylimidizole and tetrazole. A hydroxyl group may then be substituted again for the dimethoxytrityl group in the dimethoxytrityl resin to provide for the addition of other nucleotides in the resin support. This procedure may be repeated to provide polynucleotides with extended chains of nucleotides.

In the drawings:

FIG. 3 is a table of successive steps involved in preparing the polynucleotide shown in FIG. 2;

Figure 1:
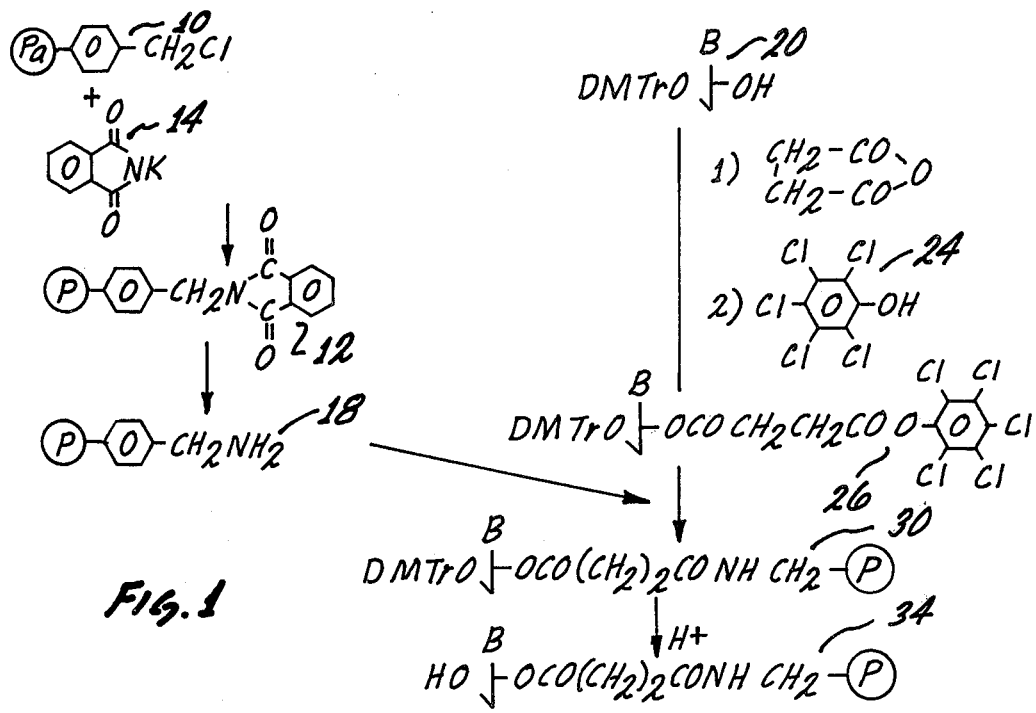
FIG. 1 is a flow chart of chemical reactions for producing a mononucleotide with a resin support.
Figure 2:
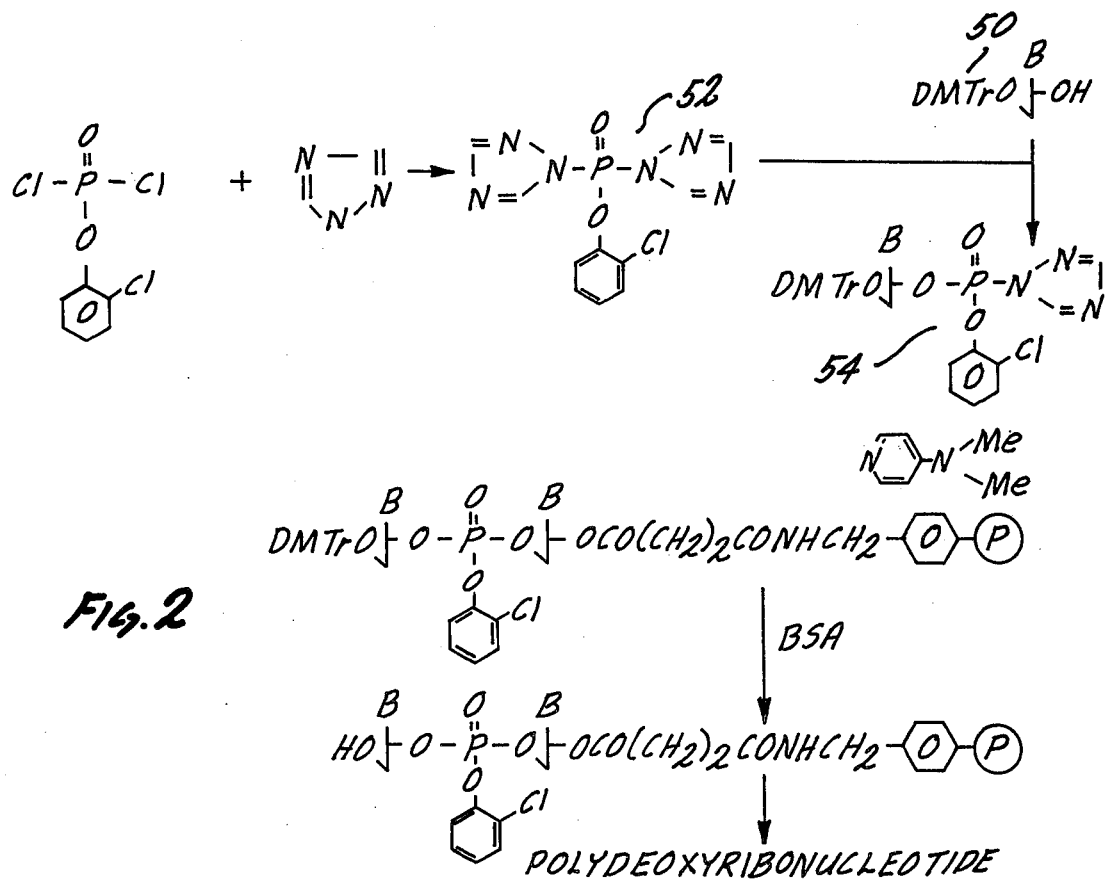
FIG. 2 is a flow chart of chemical reactions for adding nucleosides to the mononucleotide produced in accordance with the flow chart shown in FIG. 1 to obtain a polynucleotide.

FIG. 4 constitutes graphs showing the optical density of different polynucleotides produced in accordance with the method constituting this invention;

FIG. 5 is a table showing the efficiency in adding successive nucleotides to the resin-supported mononucleotide by the method constituting this invention.

In the method of this invention, a suitable resin support is first provided. This may be accomplished by initially providing a suitable resin such as a commercially available chloromethyl-polystyrene 10 (1.06 mimole of Cl/g) designated commercially as Merrifield resin. Such a polystyrene may have approximately one percent (1%) or two percent (2%) of divinyl benzene cross linked with the polystyrene.

The chloromethyl-polystyrene may be converted to a phthalimido methyl resin 12 by treatment with potassium phthalimide 14. The phthalimido methyl resin 12 is then converted to an amino methyl resin 18 by treatment with hydrazine in ethanol.

A 5'-O-dimethoxytrityl deoxynucleotide 20 is reacted with succinic anhydride 21 (1.5 mol equivalent) in the presence of 4-dimethylamino pyridine (1.5 mol equivalent)) in pyridine at a suitable temperature such as room temperature for an extended period of time (such as overnight). The result of this reaction is a monocusuccinate derivative in a yield of approximately eighty percent (80%).

The monosuccinate derivative is then treated with pentachlorophenol 24 (1.1 mol equivalent) and dicyclohexylcarbodimide (3 mol equivalent) in dimethylformamide at a suitable temperature such as room temperature for an extended period of time such as approximately twenty (20) hours. As a result of this treatment, an activated ester 26 is obtained in a yield of approximately ninety percent (90%). It is possible that other materials may be used than pentachlorophenol to obtain the activated ester 26 but the time for the reaction may be slowed.

The activated ester 26 (2.5 mol equivalent) is then treated with the amino methyl resin 18 to provide an amino bonded resin support 30. This treatment may be provided in triethylamine (2.75 mol equivalent) in dimethyl formamide. The mixture may be shaked at a suitable temperature such as room temperature for an extended period of time such as approximately twenty (20) hours to provide the amino-bonded resin support 30, which includes a dimethoxytrityl group.

Any unreacted amino group in the resin support 30 may be masked by treatment with phenyl isocyanate (10% solution in pyridine) at a suitable temperature such as room temperature for an extended period of time such as approximately one (1) hour. The dimethoxytrityl group in the resin support 30 may be removed by treatment with a two percent (2%) solution of benzenesulfonic acid in $CHCl_3$-MeOH at a suitable temperature such as room temperature for a relatively short period such as thirty (30) seconds. In this way, a nucleoside 34 is obtained. The nucleoside serves as a support for the attachment of additional nucleotides by the method of this invention to form a polynucleotide.

The method above described is disclosed in detail in the following articles published by scientists who were employees of the assignee of record of this patent application at the time that such articles were published:

(1) "Solid-phase synthesis of Hentriacontanucleotide" by Piotr Dembek, Ken-ichi Miyoshi and Keiichi Itakura;

(2) "Solid-phase synthesis of polynucleotides. IV. Usage of polystyrene resins for the synthesis of polydeoxyribonucleotides by the phosphotriester method" by Ken-ichi Miyoshi, Rene Arentzen, Ting Haung and Keiichi Itakura.

The first article was published in the Journal of the American Chemical Society in 1981 at Volume 103, pages 706–708 and the second article was published in Nucleic Acids Research in Volume 8 Number 22 1980 on pages 5507 through 5518.

FIG. 3 indicates the steps for removing the dimethoxytrityl group from the resin support 30. The support may be initially washed with pyridine, as shown in Step 1 of FIG. 3, and the 5'-hydroxyl group may then be masked with a ten percent (10%) solution of acetic anhydride, as shown in step 2 of FIG. 3. The resin support may then be washed with pyridine (Step 3 of FIG. 3) and may be subsequently washed a particular number of times (such as 3 times) with a $CHCl_3$-MeOH (7:3 v/v) solution which has been pre-cooled to a suitable temperature such as 0° C. This has been shown in Step 4 of FIG. 3. The dimethoxytrityl resin may be shaken with the pre-cooled solution of $CHCl_3$-MeOH to cool and swell the resin.

The resin support is then treated with a two percent (2%) solution of benzenesulfonic acid in $CHCl_3$-MeOH (7:3 v/v, 10 ml). This treatment is shown in Steps 5 and 6 of FIG. 3. The treatment may occur for a suitable period of time such as approximately one (1) minute under a vigorous shaking. The nucleotide may then be washed in a suitable material such as pyridine. Such washing is illustrated in Steps 7 and 8 of FIG. 3. By this procedure, the dimethoxytrityl group is completely removed without harming the adenine residue in oligonucleotides.

Step 9 of FIG. 3 illustrates in a concise form the method of applicants for adding nucleotides to the resin support 32 to obtain a polynucleotide. In this step, "THF" is intended to mean tetrahydrofurane and "DMAP" is intended to mean dimethylamino pyridine. This procedure will be described in detail subsequently.

As a first step in attaching the additional nucleotides, a 3'-hydroxyl nucleoside 50 is phosphorylated with O-chlorophenyl phosphoroditriazolide 52 in dioxane or hydrofurane for an extended period such as approximately two (2) hours. This causes a monotriazolide 54 to be produced.

The phosphoroditriazolide 52 may be prepared by providing a mixture of triazole (1.05 g, 15 mmole) and O-chlorophenyl phosphorodichloridate (1.27 g, 5 mmole) in tetrahydrofurane (20 ml). To this mixture is added triethylamine (1.10 g, 11 mmole) in tetrahydrofurane (20 ml) at a suitable temperature such as 0° C. The reaction mixture may then be shaken for a suitable period of time such as approximately one (1) hour.

The mixture described in the previous paragraph may then be filtered. The filtrate containing 0.125 mmole/ml of the phosphoroditriazole 52 can be stored for an extended period as long as one (1) week at a suitable temperature such as 0° C. To produce the monotriazolide 54, the phosphoroditriazole 52 (4.8 ml, 0.6 mmole) can be reacted with the 5'-O-dimethoxytrityl-3'-hydroxyl deoxynucleoside 50. The deoxynucleoside may be evaporated twice with pyridine before reaction with the phosphoroditriazole 52.

The monotriazolide 54 may then be coupled to the nucleoside 34 in the presence of a nucleophilic agent such as a chemical selected from a group consisting of dimethylaminopyridine, N'-methylimidazole and tetrazole.

In the coupling reaction in materials such as dioxane, the coupling reaction between the nucleoside 34 and the coupling agent 54 generally requires six (6) hours to obtain a ninety percent (90%) yield of phosphotriester bonds on the resin. In the presence of dimethylaminopyridine, however, a yield of ninety percent (90%) may be obtained in a shortened period of time such as approximately three (3) hous. When the reaction occurs in tetrahydrafurane with dimethylaminopyridine, the reaction may occur almost to completion in a time as short as approximately two (2) hours under substantially the same conditions. This significant solvent effect can be caused by either (or both) the changing of the catalytic effect of the dimethylaminopyridine or the physical factors of the resins in different solvents.

The procedure described above can be repeated to couple additional nucleotides to the nucleoside 34. Specifically, the nucleosides can be phosphorylated as described above to produce the monotriazolide 54. The monotriazolide 54 can then be combined with the nucleoside 34 as described above to produce a resin support having a dimethoxytrityl group. Although only mononucleotides have been coupled in this manner, there is ample reason to believe that dinucleotides and trinucleotides can be coupled in a similar manner.

The method described above is fully disclosed in an article entitled "Solid-phase synthesis of polynucleotides. V. Synthesis of oligodeoxyribonucleotides by the phosphomonotriazolide method" published by Ken-ichi Miyoshi and Keiichi Itakura, both at that time employed by the assignee of record of this patent application. This article is published in "Nucleic Acid Research" as Symposium Series No. 7 1980 at pages 281 through 292.

FIG. 4 illustrates the relationship between the time in minutes and the optical densities of the successive nucleosides which have been produced in different polynucleotides by the methods of this invention. FIG. 4(A) illustrates the attachment of thirteen (13) thymidine residues (bases) to the resin support. This result was obtained by a hplc profile on a Permaphase AAX column after removal of all of the protecting groups. FIG. 4(B) illustrates the attachment of eleven (11) nucleotides to the resin support in the sequence of TGCACCATTCT. FIG. 4(C) illustrates the attachment of twelve (12) nucleotides to the resin support in the sequence of TGGAGCCACTAT.

The coupling yield by percentage for each of the nucleotides in the polynucleotides of FIG. 4 is illustrated in FIG. 5. The first row (designated as "dT14") illustrates the coupling yield by percentage in each cycle involved in the production of the polynucleotide of FIG. 4(A). The second row (designated as "dodecamer") indicates the coupling yield by percentage in each cycle involved in the production of the polynucleotide of FIG. 4(C). The third row (designated as "undecamer") indicates the coupling yield by percentage in each cycle involved in the production of the polynucleotide of FIG. 4(B). As will be seen, the coupling yield in each cycle involved in the production of the polynucleotides of FIGS. 4(A), 4(B) and 4(C) is quite large.

The methods described above are also advantageous when used with silica gel as the resin support. Silica gel is advantageous as a resin support because it does not swell when mixed with various solvents. Silica gel is also advantageous because the reaction with silica gel tend to occur at a relatively fast rate with silica gel.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. A method of forming a polynucleotide, including the following steps:
providing a resin support,
phosphorylating a nucleoside to provide a monotriazolide,
combining the monotriazolide with the resin support to provide a dimethoxytrityl resin, and
substituting a hydroxyl group for the dimethoxytrityl group in the dimethoxytrityl resin to provide the polynucleotide.

2. The method set forth in claim 1 wherein
the nucleoside is a 3'-hydroxyl nucleoside and
the 3'-hydroxyl nucleoside is phosphorylated with a phosphoroditriazolide to obtain the monotriazolide and
the monotriazolide is combined with the resin support in the presence of a nucleophilic catalyst to provide the dimethoxytrityl resin.

3. The method set forth in claim 3 wherein
the nucleophilic catalyst is selected from a group consisting of dimethylaminopyridine, N'-methylimidazole and tetrazole and
the resin in the resin support is a polystyrene.

4. The method set forth in claim 3 wherein
the hydroxyl group is substituted for the dimethoxytrityl group in a solution of benzenesulfonic acid.

5. The method set forth in claim 1 wherein
the resin support is obtained by forming an amino benzyl resin and combining this resin with an activated ester of a nucleoside.

6. A method of forming a polynucleotide, including the following steps:
providing a resin support,
phosphorylating a 3'-hydroxyl nucleoside in a phosphoroditriazolide to form a monotriazolide,
combining the monotriazolide and the resin support in the presence of a nucleophilic catalyst to provide a dimethoxytrityl resin, and
removing the dimethoxytrityl group from the dimethoxytrityl resin in the presence of a suitable agent.

7. The method set forth in claim 6 wherein
the dimethoxytrityl resin is treated with benzenesulphonic acid.

8. The method set forth in claim 5 wherein
the phosphorylation of the 3'-hydroxyl nucleoside is performed in dioxane or tetrafurane and
the nucleophilic agent in the step of providing the dimethoxytrityl resin is selected from a group consisting of dimethylaminopyridine, N'-methylimidazole and tetrazole.

9. The combination set forth in claim 8 wherein the dimethylaminopyridine is mixed with tetrahydrofurane in the production of the dimethoxytrityl resin.

10. The method set forth in claim 9 wherein
the resin support system is obtained by forming an amino hydroxyl resin and combining this resin with an activated ester of a nucleoside.

11. A method set forth in claim 9 wherein
the resin support is obtained by treating chloromethyl polystyrene with potassium pthalimide to obtain a pthalimidomethyl-resin and
the pthalimidomethyl-resin is converted into the amino-resin by treatment with hydrazine in ethanol and
a 5'-O-dimethoxytrityl deoxynucleotide is reacted with succinic anhydride to form a monosuccinate derivative and
the monosuccinate derivative is treated with pentachlorophenol to form a pentachlorophenol-treated nucleoside,
the amino-resin is combined with the pentachlorophenol-treated nucleoside to obtain an amino-bonded resin support.

12. In a method of producing a polynucleotide, the steps of:
providing a resin support
phosphorylating a 3'-hydroxyl nucleoside in phosphoroditriazolide in the presence of a material selected from a group consisting of dioxane and hydrofurane to form a monotriazolide, and
combining the monotriazolide and the resin support in the presence of a nucleophilic catalyst to provide a dimethoxytrityl resin.

13. In the method set forth in claim 12,
the nucleophilic catalyst constituting a material selected from a group consisting of dimethylaminopyridine, N'-methylimidazole and tetrazole.

14. In the method set forth in claim 13,
the phosphoroditriazolide constituting O-chlorophenyl phosphoroditriazolide.

15. In the method set forth in claim 12,
the nucleophilic catalyst consisting of dimethylaminopyridine in tetrafurane.

16. In the method set forth in claim 12,
the resin in the resin support constituting polystyrene.

17. In a method of producing a polynucleotide, the steps of:
providing a resin-supported nucleoside,
combining a monotriazolide and the resin-supported nucleoside in the presence of a nucleophilic catalyst to provide a dimethoxytrityl resin, and
substituting the dimethoxytrityl group in the dimethoxytrityl resin with a hydroxyl group to form the polynucleotide.

18. In the method set forth in claim 17,
the nucleophilic catalyst being selected from a group consisting of dimethylaminopyridine, N'-methylimidazole and tetrazole.

19. In the method set forth in claim 17,
the nucleophilic catalyst constituting dimethylaminopyridine in tetrafurane.

20. In the method set forth in claim 17,
the substitution of the hydroxyl group for the dimethoxytrityl group in the dimethoxytrityl resin occurring in a solution of benzenesulfonic acid in chloroformmethanol.

21. In the method set forth in claim 20,
the nucleophilic agent being selected from a group consisting of dioxane, dimethylaminopyridine or a combination of dimethylaminopyridine and tetrahydrofurane and the substitution of the hydroxyl group for the 3'-dimethoxytrityl group in the dimethoxytrityl resin occurring in a solution of benzenesulfonic acid in chloroformamethanol.

22. In the method set forth in claim 17,
the nucleophilic catalyst being selected from a group consisting of dimethylaminopyridine, N'-methylimidazole and tetrazole.

23. In a method of producing a polynucleotide, the steps of:
phosphorylating a 3'-hydroxyl nucleoside with a phosphoroditriazolide to provide a monotriazolide.

24. The method set forth in claim 23 wherein
the phosphoditriazolide is a O-chlorophenyl phosphoditriazolide and the phosphorylation occurs in a material selected from a group consisting of dioxane and tetrahydorfurane.

25. A method of forming a polynucleotide, including the following steps:
(a) providing an amino-resin,
(b) providing a chlorophenolated nucleoside,
(c) combining the amino-resin with the chlorophenolated nucleoside to obtain an amino-bonded resin support,
(d) phosphorylating a nucleoside to obtain a monotriazolide,
(e) combining the monotriazolide with the amino-bonded resin support to provide a dimethoxytrityl resin, and
(f) substituting a hydroxyl group for the dimethoxytrityl group in the dimethoxytrityl resin to provide a polynucleotide.

26. The method set forth in claim 25 wherein
steps (c) and (d) are repeated to add additional nucleotides to the polynucleotide.

27. The method set forth in claim 25 wherein
the phosphorylation in step (c) is provided by combining the nucleoside with a phosphoroditriazolide and step (d) is performed in the presence of a nucleophilic agent.

28. The method set forth in claim 27 wherein
the phosphorylation in step (c) is performed in dioxane or tetrafurane and
the nucleophilic agent in step (d) is selected from a group consisting of dimethylaminopyridine, N'-methylimidazole and tetrazole.

29. The method set forth in claim 26 wherein the resin is a polystyrene.

30. The method set forth in claim 26 wherein the resin is a silica gel.

31. A method of forming a polynucleotide, including the following steps:
(a) treating chloro-methyl polystyrene with potassium pthalimide to obtain a phthalimidomethyl-resin,
(b) treating the phthalimidomethyl-resin with hydrazine in ethanol to obtain an amino-resin,
(c) reacting the amino-resin with a pentachlorophenolated nucleoside to obtain an amide-bonded resin,
(d) phosphorylating the nucleoside in a phosphoroditriazolide to form a monotriazolide,
(e) combining the monotriazolide and the amide-bonded resin support in the presence of a nucleophilic agent to provide a dimethoxytrityl resin, and
(f) removing the dimethoxytrityl group from the dimethoxytrityl resin in the presence of a suitable agent.

32. The method set forth in claim 31 wherein
steps (d), (e) and (f) are repeated to attach additional nucleosides to the amide-bonded resin.

33. The combination set forth in claim 32 wherein step (d) is performed in dioxane or tetrafurane.

34. The method set forth in claim 32 wherein
the nucleophilic agent is selected from a group consisting of dimethylaminopyridine, N'-methylimidazole and tetrazole.

35. The method set forth in claim 33 wherein
the nucleophilic agent is dimethylaminopyridine mixed with tetrahydrofurane.

36. The polynucleotide produced by the method set forth in claim 1.

37. The polynucleotide produced by the method set forth in claim 3.

38. The polynucleotide produced by the method set forth in claim 6.

39. The dimethoxytrityl resin produced by the method set forth in claim 12.

40. The polynucleotide produced by the method set forth in claim 25.

41. The polynucleotide set forth in claim 29.

42. The polynucleotide produced by the method set forth in claim 31.

43. The method set forth in claim 3 wherein
the resin is silica gel.

44. The resin support for a polynucleotide comprising an amide bonded polystyrene resin support.

45. In the method set forth in claim 17, the nucleophilic catalyst constituting dioxane.

46. In the method set forth in claim 19, the resin constituting polystyrene or silica gel.

47. In the method set forth in claim 44, the resin constituting polystyrene or silica gel.

48. The method set forth in claim 23 wherein
the monotriazolide is coupled to a nucleoside to provide a dimethoxytrityl deoxynucleotide.

49. The method set forth in claim 17 wherein the resin support is provided by the following steps:
(a) treating chloro-methyl polystyrene with potassium pthalimide to obtain a phthalimidomethyl-resin,
(b) treating the phthalimidomethyl-resin with hydrazine in ethanol to obtain an amino-resin,
(c) reacting the amino-resin with a pentachlorophenolated nucleoside to obtain an amino-bonded resin.

50. The polynucleotide produced by the method of claim 17.

51. The polynucleotide produced by the method of claim 46.

* * * * *

Notice of Adverse Decisions in Interference

In Interference No. 101,725, involving Patent No. 4,401,796, Keiichi Itakura, SOLID-PHASE SYNTHESIS OF POLYNUCLEOTIDES, final judgement adverse to the patentee was rendered June 11, 1991, as to claims 1, 2, 5-10, 12-15, 17-28, 30-43, 45-48, 50 and 51.

*(Official Gazette Oct. 22, 1991)*